(12) United States Patent
Agarwal

(10) Patent No.: US 9,161,982 B2
(45) Date of Patent: Oct. 20, 2015

(54) SANITIZER COMPOSITIONS COMPRISING ALCOHOL AND AN ANTIMICROBIAL EFFICACY ENHANCER

(71) Applicant: VI-JON, INC., St. Louis, MO (US)

(72) Inventor: Namita Agarwal, Ballwin, MO (US)

(73) Assignee: Vijon, Inc., St. Louis, MO (US)

( * ) Notice: Subject to any disclaimer, the term of this patent is extended or adjusted under 35 U.S.C. 154(b) by 0 days.

(21) Appl. No.: 13/917,868

(22) Filed: Jun. 14, 2013

(65) Prior Publication Data

US 2013/0338236 A1 Dec. 19, 2013

Related U.S. Application Data

(60) Provisional application No. 61/661,042, filed on Jun. 18, 2012.

(51) Int. Cl.

| | |
|---|---|
| *A61K 47/12* | (2006.01) |
| *A61K 31/045* | (2006.01) |
| *A61K 47/10* | (2006.01) |
| *A61L 2/18* | (2006.01) |
| *A61K 8/34* | (2006.01) |
| *A01N 31/02* | (2006.01) |
| *A61K 8/37* | (2006.01) |
| *A61Q 17/00* | (2006.01) |

(52) U.S. Cl.
CPC .............. *A61K 47/12* (2013.01); *A01N 31/02* (2013.01); *A61K 8/34* (2013.01); *A61K 8/375* (2013.01); *A61K 31/045* (2013.01); *A61K 47/10* (2013.01); *A61Q 17/005* (2013.01)

(58) Field of Classification Search
CPC ..... A61K 47/12; A61K 31/045; A61K 47/10; A61K 8/34; A61K 8/375; A61K 17/005; A61K 31/02
See application file for complete search history.

(56) References Cited

U.S. PATENT DOCUMENTS

| 4,695,453 | A | 9/1987 | Tuominen et al. |
|---|---|---|---|
| 8,318,654 | B2 | 11/2012 | Hoffman et al. |
| 2002/0022660 | A1 | 2/2002 | Jampani et al. |
| 2003/0139307 | A1 | 7/2003 | Narula et al. |
| 2003/0152644 | A1 | 8/2003 | Modak et al. |
| 2006/0039942 | A1 | 2/2006 | Greten et al. |
| 2006/0251690 | A1 | 11/2006 | Lipshutz et al. |
| 2007/0184013 | A1 | 8/2007 | Snyder et al. |
| 2007/0265352 | A1 | 11/2007 | Roeding et al. |
| 2007/0281999 | A1 | 12/2007 | Fox et al. |
| 2009/0012174 | A1 | 1/2009 | Seitz, Jr. et al. |
| 2011/0117048 | A1 | 5/2011 | Kritzler |
| 2012/0141600 | A1 | 6/2012 | Taylor et al. |
| 2013/0052156 | A1 | 2/2013 | Snyder et al. |

FOREIGN PATENT DOCUMENTS

| WO | 01/41727 A1 | 6/2001 |
|---|---|---|
| WO | 2010147868 A2 | 12/2010 |

OTHER PUBLICATIONS

International Search Report and Written Opinion for Application No. PCT/US2013/045812, mailed Feb. 16, 2015, 13 pgs.
International Preliminary Report on Patentability for Application No. PCT/US2013/045812, mailed Mar. 19, 2015, 9 pgs.

*Primary Examiner* — Renee Claytor
(74) *Attorney, Agent, or Firm* — Armstrong Teasdale LLP

(57) ABSTRACT

The present invention provides alcohol-based sanitizers containing an efficacy enhancer for improved antimicrobial effectiveness. The present invention further provides skin sanitization methods comprising contacting skin having microbial contamination with an antimicrobial composition comprising an alcohol and an efficacy enhancer to achieve a minimum 3 $\log_{10}$ reduction in skin pathogen contamination after one application.

16 Claims, No Drawings

SANITIZER COMPOSITIONS COMPRISING ALCOHOL AND AN ANTIMICROBIAL EFFICACY ENHANCER

BACKGROUND OF THE INVENTION

The field of the invention relates generally to antimicrobial sanitizers.

Alcohol-based sanitizers have found increasing use by consumers and institutional facilities due to the capability to quickly kill microbes without the use of soap and water. Pathogenic microbes are typically transmitted by person-to-person or object-to-person contact. The probability of transmission increases when personal hygiene, such as hand washing, is inadequate. Hand washing with soap and water provides an effective method for reducing the potential for microbe transmission and contamination, but it is not always practical or feasible to sanitize the skin in this manner. Alcohol-based hand sanitizers can be used to sanitize the hands in such cases, or can be used as a supplement to soap and water.

Alcohol-based sanitizers are effective against many types of pathogenic microbes including antibiotic resistant bacteria, tuberculosis, flu viruses, cold viruses, human immunodeficiency virus, and fungi. Alcohol is typically efficacious at skin contact times of less than a minute. For this reason, alcohol-based hand sanitizers are extensively used in hospitals as an alternative to antiseptic soaps, and have two general applications: hygienic hand cleaning and surgical hand disinfection. Alcohol based hand cleaning compositions provide a better skin tolerance as compared to antiseptic soap and have been shown to have more effective anti-pathogen properties as compared to antiseptic soaps.

Problematically, alcohol-based sanitizers are generally effective only during contact time and have little or no residual effect. Because the sanitizers do not achieve complete germ kill, recolonization of pathogenic microbes after sanitizer application can occur. Further, recurrent use of alcoholic sanitizers may leave a biofilm on the skin surface that may entrap pathogenic microbes resulting in decreased effectiveness with added use in the absence of hand washing with soap.

Therefore, there is a need for improved alcohol-based hand sanitizers that provide for increased antimicrobial effectiveness after multiple applications.

BRIEF DESCRIPTION OF THE INVENTION

Briefly, the present invention provides alcohol-based sanitizers containing an efficacy enhancer for improved antimicrobial effectiveness.

In one aspect, the antimicrobial compositions comprise from about 50% by weight to about 95% by weight of at least one $C_{1-6}$ alcohol and from about 0.1% by weight to about 5% by weight of an efficacy enhancer. The efficacy enhancer comprises:

(i) a monoglyceride of formula (1), formula (2) or a combination thereof

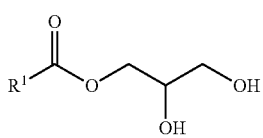

(1)

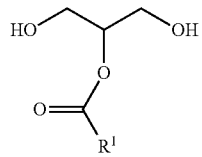

(2)

wherein $R^1$ is a $C_{5-23}$ straight or branched chain hydrocarbyl or substituted hydrocarbyl;

(ii) a diglyceride of formula (3), formula (4) or a combination thereof

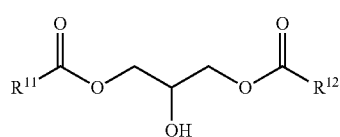

(3)

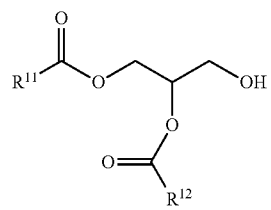

(4)

wherein $R^{11}$ and $R^{12}$ are independently selected from a $C_{5-23}$ straight or branched chain hydrocarbyl or substituted hydrocarbyl;

(iii) an aromatic alcohol of formula (5)

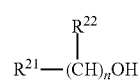

(5)

wherein $R^{21}$ is selected from the group consisting of phenyl, naphthyl and thienyl, and each $R^{22}$ is independently selected from hydrogen and $C_{1-6}$ hydrocarbyl or substituted hydrocarbyl, and n is an integer from 1 to 6;

(iv) an aromatic glycol ether of formula (6)

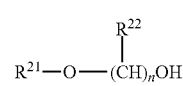

(6)

wherein $R^{21}$ is selected from the group consisting of phenyl, naphthyl and thienyl, each $R^{22}$ is independently selected from hydrogen and $C_{1-6}$ hydrocarbyl or substituted hydrocarbyl, and n is an integer from 1 to 6; or (v) a combination thereof.

In another aspect, a skin sanitation method is provided. The method comprises contacting skin having microbial contamination with an antimicrobial composition comprising from about 50% by weight to about 95% by weight of at least one $C_{1-6}$ alcohol and from about 0.1% by weight to about 5% by weight of an efficacy enhancer. The efficacy enhancer comprises:

(i) a monoglyceride of formula (1), formula (2) or a combination thereof

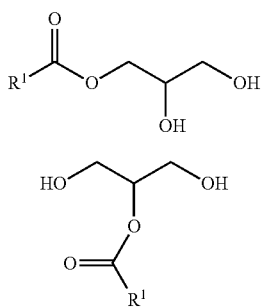

wherein $R^1$ is a $C_{5-23}$ straight or branched chain hydrocarbyl or substituted hydrocarbyl;

(ii) a diglyceride of formula (3), formula (4) or a combination thereof

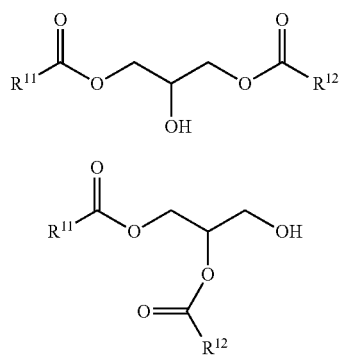

wherein $R^{11}$ and $R^{12}$ are independently selected from a $C_{5-23}$ straight or branched chain hydrocarbyl or substituted hydrocarbyl;

(iii) an aromatic alcohol of formula (5)

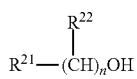

wherein $R^{21}$ is selected from the group consisting of phenyl, naphthyl and thienyl, and each $R^{22}$ is independently selected from hydrogen and $C_{1-6}$ hydrocarbyl or substituted hydrocarbyl, and n is an integer from 1 to 6;

(iv) an aromatic glycol ether of formula (6)

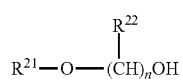

wherein $R^{21}$ is selected from the group consisting of phenyl, naphthyl and thienyl, each $R^{22}$ is independently selected from hydrogen and $C_{1-6}$ hydrocarbyl or substituted hydrocarbyl, and n is an integer from 1 to 6; or (v) a combination thereof.

The antimicrobial composition provides a minimum log 10 reduction in skin pathogen contamination after one application as measured by ASTM Method E-2755-10 protocol.

In another aspect, the antimicrobial compositions provide a $\log_{10}$ reduction in skin pathogen contamination after ten applications greater than the $\log_{10}$ reduction in skin pathogen contamination after one application.

DETAILED DESCRIPTION OF THE INVENTION

In accordance with the present invention, there is provided, as described herein, skin sanitizer compositions having improved antimicrobial efficacy, the compositions comprising alcohol and an efficacy enhancer. Skin sanitization methods are also provided.

It has been discovered that certain compounds act as efficacy enhancers to improve the rapid antimicrobial efficacy of alcohol-based sanitizers. These compounds also exhibit weak to moderate preservation properties. "Preservatives" as defined herein are substances that may be added to personal care products for the purpose of inhibiting the development of micro-organisms in such products, wherein the preservative effect is typically exhibited in 1 to 3 days or longer. Preservatives do not exhibit a rapid efficacy or sufficient lethality needed to produce a $\log_{10}$ kill of existing microbes that is required by hand sanitizers. The discovery that such preservative compounds improve the rapid microbial kill properties of alcohol-based sanitizers is surprising because preservatives are not known to possess such rapid antimicrobial efficacy properties.

The sanitizers of the present invention comprise at least one $C_{1-6}$ alcohol. Examples of suitable alcohols include methanol, ethanol, propanol, butanol, pentanol, hexanol, isomers thereof, and mixtures thereof. In some embodiments, the alcohol is methanol, ethanol, n-propanol, i-propanol, or mixtures thereof. In some other embodiments, the alcohol is ethanol, n-propanol, i-propanol or mixtures thereof. In other embodiments, the alcohol is ethanol or denatured ethanol. The alcohol content of the present sanitizers is from about 50 to about 95 percent by weight, from about 55 to about 90 percent by weight, from about 55 to about 85 percent by weight, from about 55 to about 80 percent by weight, from about 60 to about 80 percent by weight, from about 60 to about 75 percent by weight, or from about 60 to about 70 percent by weight.

In some embodiments of the present invention, the efficacy enhancer is a monoglyceride. The monoglyceride can be a 1-monoglyceride, a 2-monoglyceride, or a mixture thereof, or a mixture of monoglycerides formed from fatty acids of varying chain lengths. The monoglycerides may be of Formulae (1) and/or (2) as follows:

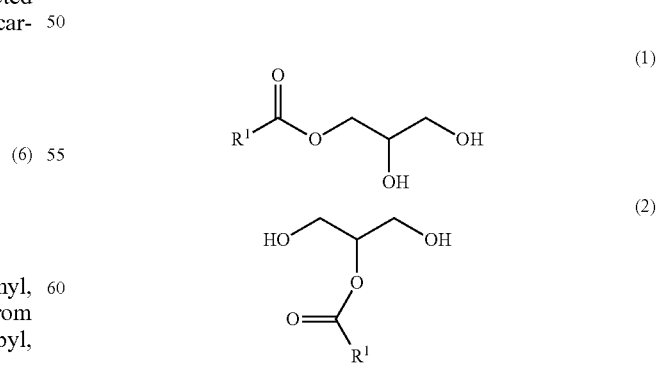

wherein $R^1$ is a $C_{5-23}$, $C_{5-21}$, $C_{5-19}$, $C_{5-17}$, $C_{5-15}$, $C_{5-13}$, $C_{5-11}$, $C_{7-15}$, $C_{9-15}$ or $C_{9-13}$ straight or branched chain hydrocarbyl or substituted hydrocarbyl. As used herein, "hydrocarbyl" is defined as compounds or moieties that are straight or branched chain, that optionally contain one or more carbon-carbon double bonds, and that consist of carbon and hydrogen. Alkyl and alkene are examples of hydrocarbyls. Substituted hydrocarbyl compounds are defined herein as hydrocarbyl compounds substituted with one or more oxygen atoms, such as hydroxyl, carboxyl, keto, aldehyde and ester moieties. Non-limiting examples of suitable monoglycerides include monoglycerides wherein the $R^1C(O)O$— is formed from stearic, palmitic, myristic, lauric, capric or caprylic acid. Non-limiting examples of suitable monoglyceride species include glyceryl monostearate, glyceryl monopalmitate, glyceryl monomyristate, glyceryl monolaurate, glyceryl monocaprate, and glyceryl monocaprylate, and mixtures thereof. In one embodiment, the monoglyceride is a mixture of glyceryl caprylate and glyceryl caprate. The monoglyceride content of the present sanitizers is from about 0.1 to about 5 percent by weight, from about 0.1 to about 3 percent by weight, from about 0.5 to about 2 percent by weight, from about 0.5 to about 1.5 percent by weight, or from about 0.75 to about 1.5 percent by weight.

In some embodiments of the present invention, the efficacy enhancer is a diglyceride. The diglyceride can be a 1,3-diglyceride, a 1,2-diglyceride, or a mixture thereof, or a mixture of diglycerides formed from fatty acids of varying chain lengths. The diglycerides may be of Formulae (3) and/or (4):

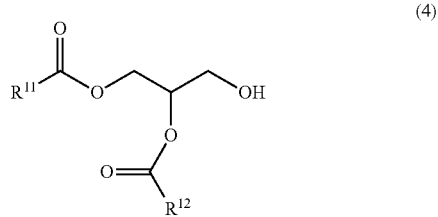

wherein $R^{11}$ and $R^{12}$ are independently a $C_{5-23}$, $C_{5-21}$, $C_{5-19}$, $C_{5-17}$, $C_{5-15}$, $C_{5-13}$, $C_{5-11}$, $C_{7-15}$, $C_{9-15}$ or $C_{9-13}$ straight or branched chain hydrocarbyl or substituted hydrocarbyl as described above. In some embodiments, $R^{11}$ and $R^{12}$ are independently selected from $C_{5-23}$, $C_{5-21}$, $C_{5-19}$, $C_{5-17}$ $C_{5-15}$, $C_{5-13}$, $C_{5-11}$, $C_{7-15}$, $C_{9-15}$ or $C_{9-13}$ straight or branched chain hydrocarbyl. Non-limiting examples of suitable diglycerides include diglycerides wherein the $R^{11}C(O)O$— and $R^{12}C(O)O$— moieties are independently formed from stearic, palmitic, myristic, lauric, capric or caprylic acid. The diglyceride content of the present sanitizers is from about 0.1 to about 5 percent by weight, from about 0.1 to about 3 percent by weight, from about 0.5 to about 2 percent by weight, from about 0.5 to about 1.5 percent by weight, or from about 0.75 to about 1.5 percent by weight.

In some other embodiments of the present invention, the efficacy enhancing compound is an aromatic alcohol and/or an aromatic glycol ether. Aromatic alcohols within the scope of the present invention are of formula (5):

and aromatic glycol ethers within the scope of the present invention are of formula (6):

wherein $R^{21}$ is selected from the group consisting of phenyl, naphthyl and thienyl, each $R^{22}$ is independently selected from hydrogen and $C_{1-6}$ hydrocarbyl and substituted hydrocarbyl as described above, and n is an integer from 1 to 6. In some embodiments, each $R^{22}$ is independently selected from hydrogen, $C_{1-6}$ hydrocarbyl and $C_{1-6}$ substituted hydrocarbyl. In some other embodiments, n is from 2 to 6 and no more than one $R^{22}$ is $C_{1-6}$ hydrocarbyl or $C_{1-6}$ substituted hydrocarbyl. Non-limiting examples of aromatic alcohols include benzyl alcohol, phenyl propanol, phenyl ethanol, phenyl butanol, phenylpentanol and phenyl hexanol. Non-limiting examples of suitable aromatic glycol ethers include 2-phenoxyethanol, 1-phenoxypropan-2-ol and 2-phenoxypropanol. The content of the aromatic alcohol and aromatic glycol ether efficacy enhancing compounds in the present sanitizers is from about 0.1 to about 3 percent by weight, from about 0.1 to about 2 percent by weight, from about 0.5 to about 2 percent by weight, from about 0.5 to about 1.5 percent by weight, or from about 0.75 to about 1.5 percent by weight.

In some embodiments, the efficacy enhancer predominantly comprises one or more monoglycerides, one or more diglycerides, one or more aromatic alcohols, or one or more aromatic glycol ethers. As used herein, "predominantly" means at least 50%, at least 75%, at least 90% or at least 95% on a w/w %, w/v % or v/v % basis. In some other embodiments, the efficacy enhancer comprises a combination of at least one monoglyceride or diglyceride and at least one aromatic alcohol or aromatic glycol ether. In such embodiments, the efficacy enhancer concentration is from about 0.1 to about 5 percent by weight, from about 0.1 to about 3 percent by weight, from about 0.5 to about 2 percent by weight, from about 0.5 to about 1.5 percent by weight, or from about 0.75 to about 1.5 percent by weight.

The sanitizers of the present invention can optionally contain other components that do not adversely affect the sanitizing effect of the present compositions. Optional components include, for instance, water, thickeners/stabilizers, moisturizers, botanicals and vitamins, colorants and/or fragrances.

In some embodiments of the present invention, thickeners, stabilizers and/or emulsifiers are optionally added to sanitizers as rheological modifiers to increase viscosity or to create gels that resist separation. Gels resist dripping after application to the skin and maximize contact time of the alcohol and efficacy enhancer on the skin. Thickeners/stabilizers are typically synthetic or natural polymers and include, for instance, cellulose (e.g., caboxymethyl cellulose and methyl cellulose), acrylamidopropyl trimonium chloride/acrylamide copolymer, and alkyl acrylate copolymer. Examples of polymers include Carbopol® Ultrez 10, Ultrez 20, Ultrez 21, 940 and 980 crosslinked polyacrylate polymers. Suitable emulsifying agents include, for instance, stearyl alcohol, sorbitan oleate, and PEG/PPG dimethicone. Suitable polymer concentrations in the sanitizer may vary with alcohol and water concentration and desired rheological properties, and is generally from about 0.05 to about 5 percent by weight, from about 0.1 to about 3 percent by weight or from about 0.1 to about 1 percent by weight. Sanitizer gel viscosity ranges from about 1,000 to about 50,000 mPa·s, from about 1,000 to about 25,000 mPa·s, about 2,000 to about 20,000 mPa·s, from about 3,000 to about 19,000 mPa·s, or from about 8,000 to about 18,000 mPa·s as measured by Brookfield RVT, 20 rpm at 25° C. When alkyl acrylate copolymers are used, suitable neutralizing agents such as triethanolamine, aminomethyl propanol, tetrahydroxypropyl ethylene diamine, triisopropanolamine, and diisopropylamine are typically included in the compositions of the present invention. In some embodiments, such as liquids or wipes, having low concentrations of, or no, added rheological modifiers, the sanitizer viscosity is less than about 1000 mPa·s, less than about 500 mPa·s, less than about 300 mPa·s, or less than about 100 mPa·s.

Humectants, conditioning and/or moisturizing agents can optionally be added to the sanitizers to soften and moisturize the skin. Humectants attract and hold water and therefore both reduce sanitizer drying time and the drying effects of alcohol on the skin. Humectants include, for instance, glycols (e.g., propylene glycol or polyethylene glycol), glycerin, glycolic acid and hyaluronic acid, with suitable concentrations thereof in the sanitizer suitably ranging from about 0.1 to about 5 percent by weight, from about 0.5 to about 3 percent by weight or from about 0.5 to about 2 percent by weight. Conditioning or moisturizing agents include, for instance, cetyl myristate, cetyl myristoleate and isopropyl myristate, with concentrations thereof in the sanitizer suitably ranging from about 0.05 percent by weight to about 2 percent by weight, from about 0.05 percent by weight to about 1 percent by weight, of from about 0.1 to about 1 percent by weight.

Other optional ingredients include botanicals and vitamins, colorants and fragrances. Botanicals include aloe vera, fenugreek, oats, flax, quince seed, cucumber, rose, comfrey and lavender. Vitamins include vitamin A (e.g., retinol, retinyl palmitate or retinyl acetate), vitamin C (e.g., ascorbyl palmitate or L-ascorbic acid), vitamin E (e.g., tocopherol or vitamin E actetate or sorbate) and vitamin B (panthenol, nicotinamide or niacin).

The sanitizer compositions of the present invention may be prepared in a variety of embodiments including liquids, gels, foams, aerosols, creams, and wipes.

The sanitizers of the present invention are believed to be effective at reducing skin contamination of a broad range of pathogens including the bacteria *Staphylococcus aureus, Staphylococcus epidermis, Escherichia coli, Pseudomonas aeruginosa, Clostridium difficile, Enterococcus faecalis, Streptococcus pneumonia* and *Salmonella choleraesuis*. It is further believed that the present sanitizers are effective against pathogenic fungi such as *Candida albicans, Aspergillis niger, Cryptococcus neoformans* and *Pneumocystis jirovecii*. It is still further believed that the present sanitizers are effective against pathogenic viruses including influenza, HIV and cold viruses.

The present sanitizers provide for at least a 2, 2.5, 3, 3.5, 4, 4.5 or 5 $\log_{10}$ reduction in pathogen microflora contamination. In some embodiments, the present sanitizers provide for a minimum 3 $\log_{10}$ reduction in pathogen contamination after one wash as measured by ASTM Standard Test Method E-2755-10 for Determining the Bacteria-Eliminating Effectiveness of Hand Sanitizer Formulations Using Hands of Adults. In other embodiments, the present sanitizers maintain a minimum 3 $\log_{10}$ reduction in pathogen contamination after 10 washes and provide more effective bacterial kill after 10 washes than after 1 wash as measured according to the ASTM Method E-2755-10 protocol. In some embodiments, the present hand sanitizers provide for a minimum 4 $\log_{10}$ reduction in pathogen contamination after 1 wash and after 10 washes. In some other embodiments, a minimum 5 $\log_{10}$ reduction is achieved after 10 washes. Therefore, the present sanitizers provide for an increased pathogen kill efficacy after successive washes. The present sanitizers are therefore more efficacious than typical alcoholic sanitizers that exhibit reduced pathogen kill efficacy after successive washes and fail to achieve a minimum 4 $\log_{10}$ reduction in pathogen contamination after 10 washes.

In some embodiments of the present invention, at least a 2, 2.5, 3, 3.5 or 4 $\log_{10}$ reduction in pathogen microflora contamination is achieved after one application (wash) of the sanitizer to the skin in a contact time of less than about a minute. Contact time is defined as the elapsed time from sanitizer application to skin dryness. In other embodiments, at least a 2, 2.5, 3, 3.5 or 4 $\log_{10}$ reduction in pathogen microflora contamination is achieved after one application (wash) of the sanitizer to the skin at a contact time of less than about 30 seconds. In other embodiments, at least a 2, 2.5, 3, 3.5, 4, 4.5 or 5 $\log_{10}$ reduction in pathogen microflora contamination is achieved after 10 successive skin washes at contact time of less than a minute each. In other embodiments, at least a 2, 2.5, 3, 3.5, 4, 4.5 or 5 $\log_{10}$ reduction in pathogen microflora contamination is achieved after 10 successive skin washes at a contact time of less than about 30 seconds each. In some other embodiments, the $\log_{10}$ reduction in microflora after 10 washes is greater than 0.2 $\log_{10}$, 0.5 $\log_{10}$ or 1 $\log_{10}$ than the $\log_{10}$ reduction after one wash, such as from 0.2 to 1.2 $\log_{10}$ greater, from 0.5 to 1.2 $\log_{10}$ greater or from 0.5 to 1 $\log_{10}$ greater.

Based on experimental data, it is believed that the antimicrobial compositions of the present invention, comprising alcohol and an efficacy enhancer, may provide greater pathogen kill efficacy as compared to an expected pathogen kill efficacy calculated from (i) the pathogen kill efficacy for a first reference composition not comprising an efficacy enhancer but otherwise having the same ingredients and alcohol concentration as the antimicrobial composition comprising the combination of alcohol and efficacy enhancer and (ii) the pathogen kill efficacy for a second reference composition not comprising alcohol but otherwise having the same ingredients and efficacy enhancer concentration as the antimicrobial composition comprising the combination of alcohol and efficacy enhancer. It is therefore believed that the efficacy enhancers of the present invention provide synergistic antimicrobial efficacy in combination with alcohol.

EXAMPLES

Example 1

Representative sanitizer formulations within the scope of the present invention were prepared and are disclosed in Tables 1a and 1b below. A sanitizer control formulation, not containing an efficacy enhancer, was also prepared as disclosed in Table 1c below. For the preparation of each sanitizer formulation, acrylate copolymer was added to water with agitation. The efficacy enhancer (glyceryl caprylate/caprate (Formula 1) or phenoxyethanol (Formula 2)) was added with agitation. Glycerin and Alcohol 40-B (denatured ethanol) were then added with agitation. Isopropylmyristate, benzophenone-4 and fragrance were then added with agitation. Finally, diisopropylamine was added with agitation to neutralize the copolymer.

TABLE 1a

Sanitizer Formula 1

| Ingredient | Concentration (% w/w) |
| --- | --- |
| Water | 28.69 |
| Acrylates/$C_{10-30}$ alkyl acrylate copolymer | 0.27 |
| Glyceryl caprylate/caprate | 1.0 |
| Glycerin | 0.99 |
| Alcohol 40-B | 68.63 |
| Isopropyl myristate | 0.2 |
| Benzophenone-4 | 0.001 |
| Fragrance | 0.15 |
| Diisopropylamine | 0.065 |

TABLE 1b

Sanitizer Formula 2

| Ingredient | Concentration (% w/w) |
| --- | --- |
| Water | 28.73 |
| Acrylates/$C_{10-30}$ alkyl acrylate copolymer | 0.24 |
| Phenoxyethanol | 1.0 |
| Glycerin | 0.99 |
| Alcohol 40-B | 68.63 |
| Isopropyl myristate | 0.2 |
| Benzophenone-4 | 0.001 |
| Fragrance | 0.15 |
| Diisopropylamine | 0.06 |

TABLE 1c

Sanitizer Control 1

| Ingredient | Concentration (% w/w) |
| --- | --- |
| Water | 29.74 |
| Acrylates/$C_{10-30}$ alkyl acrylate copolymer | 0.23 |
| Glycerin | 0.99 |
| Alcohol 40-B | 68.63 |
| Isopropyl myristate | 0.2 |
| Benzophenone-4 | 0.001 |
| Fragrance | 0.15 |
| Diisopropylamine | 0.06 |

Example 2

Antimicrobial efficacy studies were carried out following the protocol of ASTM E 2755-10 (Standard Test Method for Determining the Bacteria-Eliminating Effectiveness of Hand Sanitizer Formulations Using Hands of Adults) to determine the bacteria-eliminating effectiveness of sanitizer formulations within the scope of the present invention. Seventy-one subjects ranging in age from 18 to 74 were admitted to the study. Following a 7-day product restriction period, 66 subjects were examined physically to ensure no evidence of injury, dermatosis and/or dermatitis were present on the hands or forearms. Thirty subjects proceeded to the study. The subjects were divided into three groups of ten subjects each wherein the subjects in the first group were each treated with sanitizer Formula 1 described in Example 1, the subjects of the second group were each treated with sanitizer Formula 2 described in Example 1, and the subjects of the third group were each treated with the control sanitizer described in Example 1.

According to the protocol and testing methodology, the hands of each subject were cleansed with a 30-second hand wash with a non medicated soap followed by a 30-second water rinse. The hands of each subject were then inoculated with 0.2 mL of a suspension of approximately $1.0 \times 10^{10}$ CFU/mL of *Serratia marcescens* (ATCC #14756) and massaged gently for 30 seconds. The hands were then immediately sampled for baseline bacterial levels using a Glove Juice Sampling Procedure wherein a powder-free, sterile latex glove was placed on the subject's hand and 75 mL of sterile stripping fluid without product neutralizers was instilled into the glove. After securing the gloved wrist, the hand was massaged in a standardized manner for 60 seconds. A 5 mL sample of the liquid (glove juice) was removed from the glove, diluted and evaluated for baseline bacterial load. The subject's hands were then cleansed with a 30-second wash with the non medicated soap followed by a 30-second water rinse.

For the next ten rounds of testing, the subject's hands were inoculated as described above followed by immediate application of the test materials (i.e., the formulations under evaluation). For each product application, 2-5 mL of test material was dispensed into the cupped hands of the subjects. The subjects rubbed the test material over the entire surface of the hands and fingers and continued to rub the skin until dry. There was a minimum of 5 minutes between each testing round and hand washing was not done between rounds of testing. The subjects were sampled for residual *S. marcescens* using the above-described Glove Juice Procedure after contamination/product cycles 1, 3, 7 and 10. The samples from the $1^{st}$ and $10^{th}$ cycles were evaluated for bacterial load using the same procedure used to establish the baseline bacteria load.

The results for sanitizer Formula 1 (comprising the glyceryl caprylate/caprate efficacy enhancer), sanitizer Formula 2 (comprising the phenoxyethanol efficacy enhancer) and the control sanitizer (not containing an efficacy enhancer) are presented in Tables 2a-2c, respectively, below. Bacterial loading is reported on a $log_{10}$ basis ("Mean" column below) wherein "microbial recovery" refers to the bacterial loading of the sample in CFU/mL. A $log_{10}$ reduction was calculated as the difference between the $log_{10}$ values before and after treatment and is indicative of antimicrobial efficacy.

TABLE 2a

Sanitizer Formula 1 bacteria load results

| Sample | Sample Size | Mean | Std. Dev. | $Log_{10}$ Reduction from Baseline |
| --- | --- | --- | --- | --- |
| Baseline $Log_{10}$ Microbial Recovery | 10 | 8.99 | 0.11 | — |
| Post Application $1^{st}$ Cycle $Log_{10}$ Microbial Recovery | 10 | 4.92 | 1.20 | 4.07 |
| Post Application $10^{th}$ Cycle $Log_{10}$ Microbial Recovery | 10 | 3.81 | 0.96 | 5.18 |

TABLE 2b

Sanitizer Formula 2 bacteria load results

| Sample | Sample Size | Mean | Std. Dev. | $Log_{10}$ Reduction from Baseline |
| --- | --- | --- | --- | --- |
| Baseline $Log_{10}$ Microbial Recovery | 10 | 8.99 | 0.24 | — |
| Post Application $1^{st}$ Cycle $Log_{10}$ Microbial Recovery | 10 | 4.84 | 0.8 | 4.15 |
| Post Application $10^{th}$ Cycle $Log_{10}$ Microbial Recovery | 10 | 4.54 | 0.70 | 4.45 |

TABLE 2c

Sanitizer Control 2 bacteria load results

| Sample | Sample Size | Mean | Std. Dev. | $Log_{10}$ Reduction |
|---|---|---|---|---|
| Baseline $Log_{10}$ Microbial Recovery | 10 | 8.76 | 0.29 | — |
| Post Application $1^{st}$ Cycle $Log_{10}$ Microbial Recovery | 10 | 4.71 | 0.85 | 4.05 |
| Post Application $10^{th}$ Cycle $Log_{10}$ Microbial Recovery | 10 | 5.44 | 1.40 | 3.32 |

The data shows that the Control formulation exhibited an increase in microbial recovery from the $1^{st}$ cycle to the $10^{th}$ cycle, i.e., a reduction in antimicrobial efficacy. This is indicated by the $log_{10}$ reduction data which is indicative of the microbial kill rate and shows that the $log_{10}$ reduction value at the $10^{th}$ cycle was less than at the $1^{st}$ cycle. Therefore, the Control formulation was less efficacious with repeated treatments.

Addition of the efficacy enhancers of the present invention demonstrates that microbial recovery decreased from the $1^{st}$ cycle to the $10^{th}$ cycle, i.e., there was an increase in antimicrobial efficacy. Therefore, sanitizer formulations within the scope of the present invention were more efficacious with repeated treatments as shown by $log_{10}$ reduction values at the $10^{th}$ cycle that were greater than the values at the $1^{st}$ cycle. Because the efficacy enhancers of the present invention have preservative properties, but not rapid kill or lethality properties needed to produce a $log_{10}$ kill of existing microbes commensurate with the above testing protocol, application of a sanitizer comprising one or more efficacy enhancers in the absence of alcohol would be expected to provide an insignificant $log_{10}$ reduction in bacteria loading as compared to the experimental formulation. Based on the experimental data, it is therefore believed that the efficacy enhancers of the present invention provide synergistic antimicrobial efficacy in combination with alcohol.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An antimicrobial composition comprising:
   (a) from about 50% by weight to about 95% by weight of at least one $C_{1-6}$ alcohol; and
   (b) from about 0.1% by weight to about 5% by weight of an efficacy enhancer comprising
       a monoglyceride of formula (1), formula (2) or a combination thereof

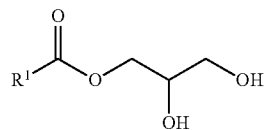

(1)

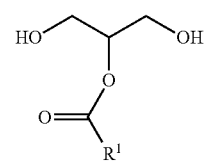

(2)

wherein $R^1$ is a $C_{5-23}$ straight or branched chain hydrocarbyl or substituted hydrocarbyl.

2. The antimicrobial composition of claim 1 wherein the alcohol is selected from the group consisting of ethanol, isopropanol, and mixtures thereof, and the alcohol concentration is from about 60% to about 75% by weight.

3. The antimicrobial composition of claim 1 wherein the efficacy enhancer predominantly comprises a monoglyceride of formula (1) or formula (2) wherein $R^1$ is selected from a $C_{7-15}$ straight or branched chain hydrocarbyl, and wherein the monoglyceride concentration is from about 0.1% to about 3% by weight.

4. The antimicrobial composition of claim 1 wherein the composition further comprises a thickener and the composition has a viscosity of from about 2,000 to about 20,000 mPa·s.

5. The antimicrobial composition of claim 1 wherein the composition is capable of providing a $log_{10}$ reduction in skin pathogen contamination after ten applications that is greater than the $log_{10}$ reduction in skin pathogen contamination after one application as measured by ASTM Method E-2755-10 protocol.

6. The antimicrobial composition of claim 1 wherein the composition is capable of providing a minimum 3 $log_{10}$ reduction in skin pathogen contamination after one application and after ten applications as measured by ASTM Method E-2755-10 protocol.

7. The antimicrobial composition of claim 6 wherein the composition is capable of achieving the $log_{10}$ reduction in skin pathogen concentration in a contact time of less than one minute.

8. The antimicrobial composition of claim 1 wherein the composition comprising the combination of alcohol and efficacy enhancer is capable of providing greater pathogen kill efficacy as compared to an expected pathogen kill efficacy calculated from (i) the pathogen kill efficacy for a first reference composition not comprising an efficacy enhancer but otherwise having the same ingredients and alcohol concentration as the antimicrobial composition comprising the combination of alcohol and efficacy enhancer and (ii) the pathogen kill efficacy for a second reference composition not comprising alcohol but otherwise having the same ingredients and efficacy enhancer concentration as the antimicrobial composition comprising the combination of alcohol and efficacy enhancer.

9. A skin sanitization method, the method comprising contacting skin having microbial contamination with an antimicrobial composition comprising:
   (a) from about 50% by weight to about 95% by weight of at least one $C_{1-6}$ alcohol; and
   (b) from about 0.1% by weight to about 5% by weight of an efficacy enhancer comprising a monoglyceride of formula (1), formula (2) or a combination thereof

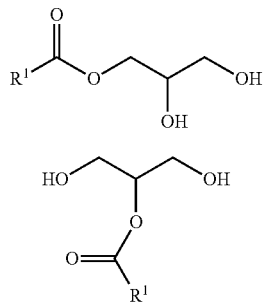

wherein $R^1$ is a $C_{5-23}$ straight or branched chain hydrocarbyl or substituted hydrocarbyl, wherein the antimicrobial composition provides a minimum 3 $\log_{10}$ reduction in skin pathogen contamination after one application as measured by ASTM Method E-2755-10 protocol.

10. The method of claim 9 wherein the alcohol is selected from the group consisting of ethanol, isopropanol, and mixtures thereof, and the alcohol concentration is from about 60% to about 75% by weight.

11. The method of claim 9 wherein the efficacy enhancer predominantly comprises a monoglyceride of formula (1) or formula (2) wherein $R^1$ is selected from a $C_{7-15}$ straight or branched chain hydrocarbyl, and wherein the monoglyceride concentration is from about 0.1% to about 3% by weight.

12. The method of claim 9 wherein the composition further comprises a thickener and the composition has a viscosity of from about 2,000 to about 20,000 mPa·s.

13. The method of claim 9 wherein the composition provides a $\log_{10}$ reduction in skin pathogen contamination after ten applications that is greater than the $\log_{10}$ reduction in skin pathogen contamination after one application.

14. The method of claim 9 wherein the composition provides a minimum 3 $\log_{10}$ reduction in skin pathogen contamination after ten applications.

15. The method of claim 9 wherein the $\log_{10}$ reduction in skin pathogen concentration is achieved in a contact time of less than one minute.

16. The method of claim 9 wherein the composition comprising the combination of alcohol and efficacy enhancer provides greater pathogen kill efficacy as compared to an expected pathogen kill efficacy calculated from (i) the pathogen kill efficacy for a first reference composition not comprising an efficacy enhancer but otherwise having the same ingredients and alcohol concentration as the antimicrobial composition comprising the combination of alcohol and efficacy enhancer and (ii) the pathogen kill efficacy for a second reference composition not comprising alcohol but otherwise having the same ingredients and efficacy enhancer concentration as the antimicrobial composition comprising the combination of alcohol and efficacy enhancer.

* * * * *